United States Patent
Aggarwal et al.

(10) Patent No.: US 11,715,554 B1
(45) Date of Patent: Aug. 1, 2023

(54) SYSTEM AND METHOD FOR DETERMINING A MISMATCH BETWEEN A USER SENTIMENT AND A POLARITY OF A SITUATION USING AN AI CHATBOT

(71) Applicant: Wysa Inc, Boston, MA (US)

(72) Inventors: Jyotsana Vempati Aggarwal, Bengaluru (IN); Chaitali Sinha, Bengaluru (IN); Megha Gupta, Bengaluru (IN)

(73) Assignee: Wysa Inc, Boston, MA (US)

(*) Notice: Subject to any disclaimer, the term of this patent is extended or adjusted under 35 U.S.C. 154(b) by 0 days.

(21) Appl. No.: 18/095,464

(22) Filed: Jan. 10, 2023

Related U.S. Application Data

(60) Provisional application No. 63/298,189, filed on Jan. 10, 2022.

(51) Int. Cl.
*G16H 20/70* (2018.01)
*G06F 40/20* (2020.01)
*G06F 40/35* (2020.01)

(52) U.S. Cl.
CPC ............. *G16H 20/70* (2018.01); *G06F 40/20* (2020.01); *G06F 40/35* (2020.01)

(58) Field of Classification Search
USPC ................................................ 704/7–10, 257
See application file for complete search history.

(56) References Cited

U.S. PATENT DOCUMENTS

| | | | | |
|---|---|---|---|---|
| 2010/0257117 | A1* | 10/2010 | Shvadron | G06F 16/313 705/36 R |
| 2013/0018957 | A1* | 1/2013 | Parnaby | G06Q 30/0203 709/204 |
| 2022/0261863 | A1* | 8/2022 | Bhan | G06Q 30/0282 |
| 2023/0021858 | A1* | 1/2023 | McReynolds | G06Q 30/016 |

* cited by examiner

*Primary Examiner* — Leonard Saint-Cyr

(57) ABSTRACT

A processor-implemented method for automatically determining a mismatch between a sentiment and a polarity of a life situation using an Artificial Intelligence (AI) model during a conversation with an AI chatbot is provided. The method includes (i) determining at least one sentiment of the user using a sentiment detecting AI model, (ii) predicting life situation from the conversation between the AI chatbot and the user using an intent recognition AI model, (ii) determining, a gravity and a polarity of the life situation using a life events scale, (iii) comparing the at least one sentiment of the user to the polarity of the life situation when the life situation is determined to the high gravity, and (iv) automatically determining the mismatch between the at least one sentiment of the user and the polarity of the at least one life situation of the high gravity situation.

20 Claims, 10 Drawing Sheets

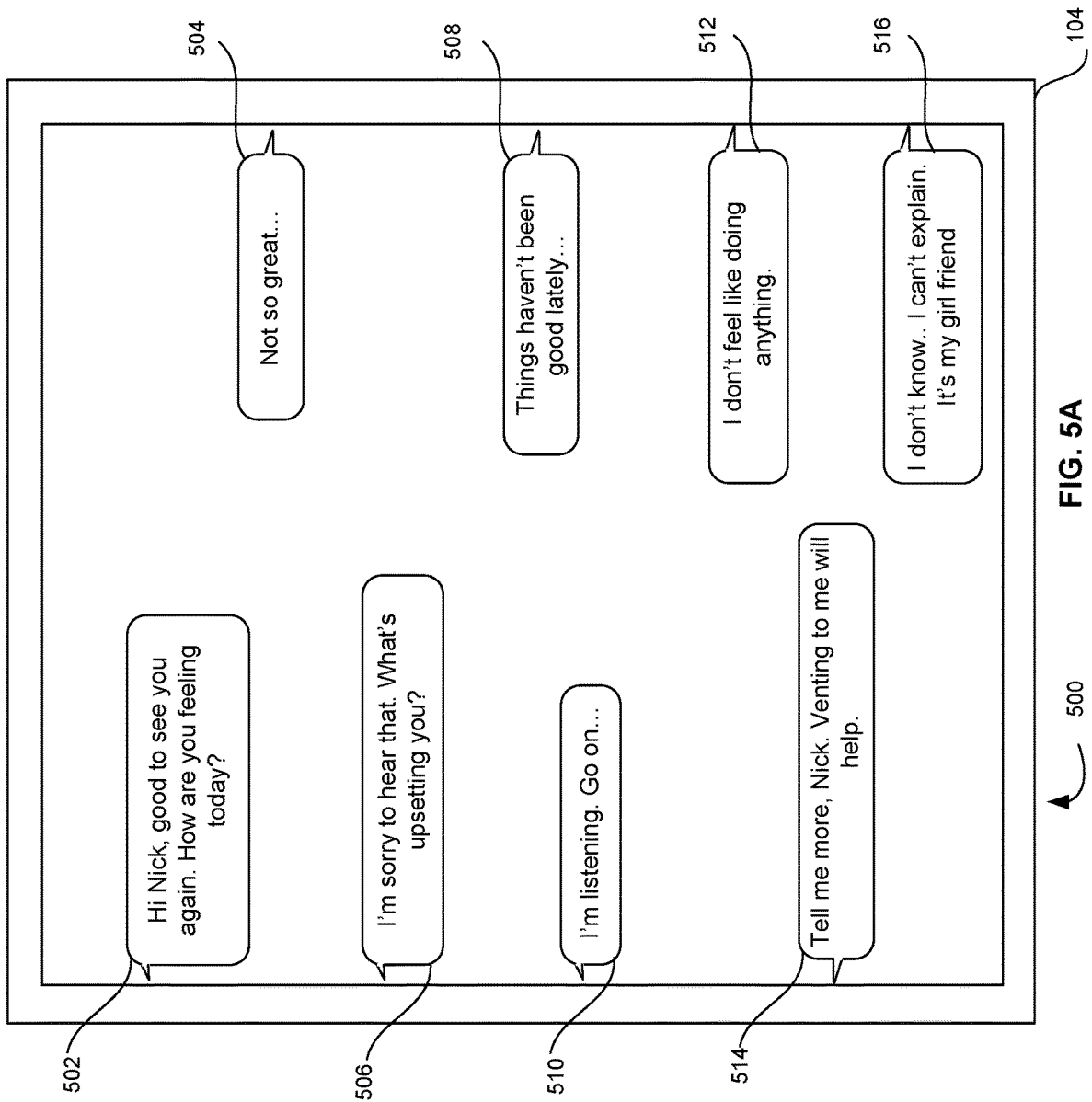

SYSTEM AND METHOD FOR DETERMINING A MISMATCH BETWEEN A USER SENTIMENT AND A POLARITY OF A SITUATION USING AN AI CHATBOT

CROSS-REFERENCE TO RELATED APPLICATIONS

This patent application claims priority to U.S. provisional patent application No. 63/298189 filed on Jan. 10, 2022, the complete disclosures of which, in their entirety, are hereby incorporated by reference.

FIELD OF THE INVENTION

Embodiments of this disclosure generally relate to an artificial intelligence (AI) chatbot, and more particularly, to a system and method for determining a mismatch between a sentiment and a polarity of a life situation using an artificial intelligence (AI) model from a conversation between an AI chatbot and the user.

BACKGROUND

A chatbot is a computer program that simulates and processes human conversation to allow a human to interact with a digital device as if it were a real person. Conversational chatbots or digital assistants leverage natural-language understanding (NLU), natural language processing (NLP), and machine learning (ML) to learn a user's preferences over time, provide recommendations, and even anticipate needs. Whereas the artificial intelligence (AI) that is used in chatbots is good at automating repetitive processes, if a demand is made that extends beyond its capabilities, the chatbot might struggle.

One application that a chatbot may be utilized for is as a personal digital assistant for mental health. The AI chatbot may engage the user in a conversation via text messages, ask questions, and facilitate getting the user to share their thoughts, feelings, etc. By doing these things, the chatbot can reduce the dependence on human experts, who may not be available on demand. Also, there is a shortage of trained professionals, and there has been an increase in the number of mental health-related challenges that people are facing today. In certain cases, the user may be going through a particularly difficult time, or they may have a mental health condition that requires a therapeutic intervention from a human expert (e.g., a therapist). In such cases, it is critical for the user to seek help from the human expert, and not just depend on the chatbot. Hence, there remains a challenge for enabling a chatbot to detect a potential mental condition of the user based on text messages exchanged between the chatbot and the user in an accurate manner.

SUMMARY

In view of the foregoing, embodiments herein provide a processor-implemented method for determining a mismatch between a sentiment and a polarity of a life situation using an Artificial Intelligence (AI) model during a conversation with an AI chatbot. The method includes (i) determining at least one sentiment of the user using a sentiment detecting AI model; (ii) predicting at least one life situation using an intent recognition AI model from the conversation between the AI chatbot and the user by (a) semantically matching at least one statement of the conversation with at least one representative statement of a life situation using the intent recognition AI model to obtain at least one semantic match, and (b) assigning a confidence score to the at least one semantic match, (iii) determining (a) a gravity of the at least one life situation as at least one of high, medium or low, and (b) a polarity of the at least one life situation as at least one of negative, neutral or positive using a life events scale, (iv) comparing the at least one sentiment of the user to the polarity of the at least one life situation when the at least one life situation is determined as high, the at least one sentiment of the user and the polarity of the at least one life situation is selected from any of a positive or a negative, and (v) automatically determining the mismatch between the at least one sentiment of the user and the polarity of the at least one life situation of high gravity.

In some embodiments, the method further includes determining the at least one life situation that is semantically close to a statement made by the user when (i) the confidence score of the at least one semantic match is above a threshold, and (ii) the at least one situation is determined to be the high gravity.

In some embodiments, the method further includes obtaining more context when the intent recognition AI model is unable to predict the at least one life situation due to confidence scores of all semantic matches of the statement by the user are less than the threshold.

In some embodiments, the AI chatbot stops to determine the mismatch when the at least one sentiment of the user and the polarity of the at least one life situation of the high gravity situation are found to be the same.

In some embodiments, the AI chatbot stops to determine the mismatch when the gravity of the at least one life situation is determined as the medium, or the low.

In some embodiments, the gravity of the at least one life situation is a measure of how much the at least one life situation is likely to influence the mood of the user, the polarity of the at least one life situation indicates whether the at least one life situation is likely to influence the mood of the user positively, negatively, or not at all.

In some embodiments, the sentiment-detecting AI model classifies the at least one sentiment of the user as one of negative, neutral, and positive using at least one of (i) rule-based methods that have a large predefined set of words and the at least one sentiment associated with each word, and combine the at least one sentiment of each word in a sentence based on certain rules; or, (ii) machine learning classifiers trained on a large dataset of sentences labeled with associated sentiment so that the machine learning classifiers learn to classify the at least one sentiment on new sentences, unseen sentences.

In some embodiments, the life events scale comprises categories of events that could occur in a user's life, the events are mapped to a potential impact on a mental health of the user.

In some embodiments, the at least one sentiment of the user is determined from at least one of (i) when the user provides a response from a set of pre-determined options for a question that is asked by the AI chatbot as how the user is feeling or (ii) an input text provided by the user.

In one aspect, one or more non-transitory computer readable storage mediums storing one or more sequences of instructions, which when executed by one or more processors, causes a method for determining a mismatch between a sentiment and a polarity of a life situation using an Artificial Intelligence (AI) model during a conversation with an AI chatbot. The method includes (i) determining at least one sentiment of the user using a sentiment detecting AI model; (ii) predicting at least one life situation using an intent recognition AI model from the conversation between the AI chatbot and the user by (a) semantically matching at least one statement of the conversation with at least one representative statement of a life situation using the intent recognition AI model to obtain at least one semantic match, and (b) assigning a confidence score to the at least one semantic match, (iii) determining (a) a gravity of the at least one life situation as at least one of high, medium or low, and (b) a polarity of the at least one life situation as at least one of negative, neutral or positive using a life events scale, (iv) comparing the at least one sentiment of the user to the polarity of the at least one life situation when the at least one life situation is determined as the high, the at least one sentiment of the user and the polarity of the at least one life situation is selected from any of a positive or a negative, and (v) automatically determining the mismatch between the at least one sentiment of the user and the polarity of the at least one life situation of high gravity situation.

In some embodiments, the method further includes determining the at least one life situation that is semantically close to a statement made by the user when (i) the confidence score of the at least one semantic match is above a threshold, and (ii) the at least one situation is determined to be the high gravity.

In some embodiments, the method further includes obtaining more context when the intent recognition AI model is unable to predict the at least one life situation due to confidence scores of all semantic matches of the statement by the user are less than the threshold.

In a second aspect, a system for determining a mismatch between a sentiment and a polarity of a life situation using an Artificial Intelligence (AI) model during a conversation with an AI chatbot is provided. The system includes a device processor and a non-transitory computer readable storage medium storing one or more sequences of instructions, which when executed by the device processor, causes a method by performing the steps. The method includes (i) determining at least one sentiment of the user using a sentiment detecting AI model; (ii) predicting at least one life situation using an intent recognition AI model from the conversation between the AI chatbot and the user by (a) semantically matching at least one statement of the conversation with at least one representative statement of a life situation using the intent recognition AI model to obtain at least one semantic match, and (b) assigning a confidence score to the at least one semantic match, (iii) determining (a) a gravity of the at least one life situation as at least one of high, medium or low, and (b) a polarity of the at least one life situation as at least one of negative, neutral or positive using a life events scale, (iv) comparing the at least one sentiment of the user to the polarity of the at least one life situation when the at least one life situation is determined as the high, the at least one sentiment of the user and the polarity of the at least one life situation is selected from any of a positive or a negative, and (v) automatically determining the mismatch between the at least one sentiment of the user and the polarity of the at least one life situation of high gravity situation.

In some embodiments, the processor is configured to determine the at least one life situation that is semantically close to a statement by the user when (i) the confidence score of the at least one semantic match is above a threshold, and (ii) the at least one situation is mapped to the high gravity situation.

In some embodiments, the processor is configured to obtain more context when the intent recognition AI model is unable to predict the at least one life situation due to confidence scores of all semantic matches of the statement by the user are less than the threshold.

In some embodiments, the AI chatbot stops to determine the mismatch when the at least one sentiment of the user and the polarity of the at least one life situation of the high gravity situation are found to be the same.

In some embodiments, the AI chatbot stops to determine the mismatch when the gravity of the at least one life situation is determined as the medium, or the low.

In some embodiments, the gravity of the at least one life situation is a measure of how much the at least one life situation is likely to influence the mood of the user, the polarity of the at least one life situation indicates whether the at least one life situation is likely to influence the mood of the user positively, negatively, or not at all.

In some embodiments, the sentiment-detecting AI model classifies the at least one sentiment of the user as one of negative, neutral, and positive using at least one of (i) rule-based methods that have a large predefined set of words and the at least one sentiment associated with each word, and combine the at least one sentiment of each word in a sentence based on certain rules; or, (ii) machine learning classifiers trained on a large dataset of sentences labeled with associated sentiment so that the machine learning classifiers learn to classify the at least one sentiment on new sentences, unseen sentences.

In some embodiments, the life events scale comprises categories of events that could occur in a user's life, the events are mapped to a potential impact on a mental health of the user.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 5A is a mock-up screenshot of a user interface that illustrates a conversation between the AI chatbot and the user when the user didn't share enough context according to some embodiments herein;

DETAILED DESCRIPTION OF PREFERRED EMBODIMENTS

Figure 1:
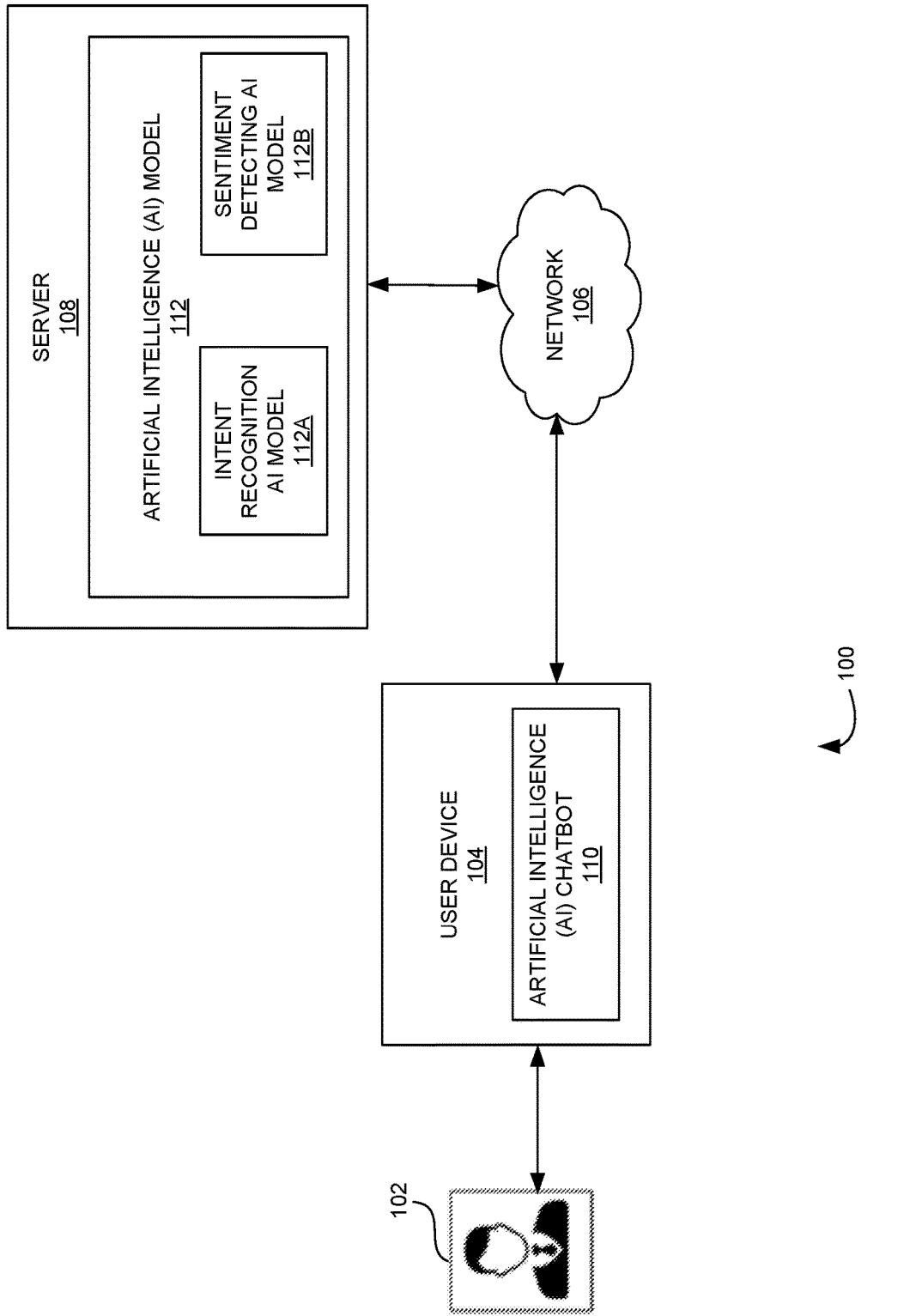
FIG. 1 is a block diagram that illustrates a system that automatically determines a mismatch between a sentiment and a polarity of a life situation using an Artificial Intelligence (AI) model during a conversation with an AI chatbot according to some embodiments herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments.

Referring now to the drawings, and more particularly to FIGS. 1 through 9, where similar reference characters denote corresponding features consistently throughout the figures, there are shown preferred embodiments.

FIG. 1 is a block diagram that illustrates a system 100 that automatically determines a mismatch between a sentiment and a polarity of a life situation using an Artificial Intelligence (AI) model 112 during a conversation with an AI chatbot 110 according to some embodiments herein. The block diagram 100 includes a user device 104 associated with a user 102, a network 106, and a server 108 that includes the artificial intelligence (AI) model 112. The AI model 112 includes an intent recognition AI model 112A, and a sentiment detecting AI model 112B. In some embodiments, the user device 104 includes the AI chatbot 110. In some embodiments, the user device 104, without limitation, may be selected from a mobile phone, a Personal Digital Assistant (PDA), a tablet, a desktop computer, or a laptop.

The user device 104 may communicate with the server 108 through the network 106. In some embodiments, the network 106 is a wired network, a wireless network, or a combination of a wired network and a wireless network. In some embodiments, the network 106 is the Internet. The server 108 starts a conversation with the user 102 through the AI chatbot 110. In some embodiments, the AI chatbot 110 is a digital assistant for mental health. The conversation includes a user input and an AI chatbot 110 input. The user input may be at least one of a text or a voice input.

The AI chatbot 110 determines an initial mood check from the conversation. The initial mood of the user 102 is checked by allowing the user 102 to select a response from a set of pre-determined options or respond using free text for a question that is asked by the AI chatbot 110 as how the user 102 is feeling. The set of pre-determined options for a question may be "Don't ask", "Not great", "Okay, I guess . . . ", "Quite good actually", and "Never been better", where "Don't ask" and "Not great" correspond to a negative initial sentiment of the user 102, "Okay, I guess . . . " corresponds to a neutral initial sentiment, and "Quite good actually" and "Never been better" correspond to a positive initial sentiment. If the user 102 is allowed to respond using free text, the sentiment-detecting AI model 112B of the server 108 determines the sentiment (positive, negative, or neutral) of the user 102 based on the response of the user 102 to the initial mood check question. In some embodiments, before training the AI model 112, the text input received from the user 102 is preprocessed that include steps such as spell correction, expansion of contractions, removal of stop words, stemming and lemmatization. The user text then needs to be vectorized so that the text is converted into a numerical representation which the AI model 112 can work with. In some embodiments, the text input is vectorized using frequency-based techniques such as Bag of Words (BoW), CountVectorizer, or TF-IDF, or semantics-based techniques such as word embeddings (eg., Word2Vec, GloVe, etc.). In some embodiments, pre-trained models from SpaCy, fastText, etc. can also be used for word embeddings. In some embodiments, the AI model 112 converts the statements of the user 102 into the text input in case of the voice input using a Natural Language Processing (NLP).

The AI model 112 predicts at least one life situation from the conversation between the AI chatbot 110 and the user 102 using the intent recognition AI model 112A. The intent recognition AI model 112A semantically matches statements of the conversation with representative statements of one or more life situations to obtain at least one semantic match. The one or more life situations are life events that are likely to affect the user 102 deeply in a positive or negative way, for example, birth or death of a family member, gaining or losing employment, starting or ending a relationship, etc. The representative statements of each life situation are statements that the user 102 might say to indicate the occurrence of that life event. For example, the life event "death of a family member" may be expressed by statements such as "I lost my dad", "My aunt passed away", "My brother is no more", etc. Similarly, the life event "gaining employment" may be expressed by statements like "I have a new job!", "I am not unemployed anymore", "I landed a job", etc.

The one or more life situations may be birth or death of a family member, start or end of one's relationship, getting or losing employment, a marriage conflict, a move, loss of a loved one, an illness, any major occurrence that can result in a lot of joy or sadness, etc. In some embodiments, when the intent recognition AI model 112A does not obtain the at least one semantic match, the AI chatbot 110 initiates a specific conversation to gather more context. The AI chatbot 110 may quit identifying the possibility of the mental health condition of the user 102 when the AI model 112 does not predict the at least one life situation.

The intent recognition AI model 112A assigns a confidence score to each semantic match between the user statement and the statements representative of various life events. The AI model 112 determines a gravity and a polarity of the at least one predicted life situation using a scale that maps different life events from highly negative to highly positive. The gravity of the at least one predicted life situation is a measure of how much the at least one predicted life situation is likely to influence the mood of the user 102. The polarity of the at least one predicted life situation indicates whether the at least one predicted life situation is likely to influence the mood of the user 102 positively, negatively, or not at all.

The AI model 112 maps the at least one predicted life situation into at least one of a high-gravity situation, a medium-gravity situation, or a low-gravity situation. The AI model 112 maps the at least one predicted life situation into at least one of a negative polarity, a neutral polarity, or a positive polarity using a life events scale.

The AI chatbot 110 encourages the user 102 to share more in order to gather more context when the intent recognition AI model 112A is unable to predict the at least one life situation when confidence scores of all semantic matches of the user statement are less than the threshold.

The AI model 112 compares at least one sentiment of the user 102 to the polarity of the at least one predicted life situation when the at least one predicted life situation is mapped to the high gravity situation. The at least one sentiment of the user 102 is classified into at least one of negative sentiment, neutral sentiment, or positive sentiment. The negative sentiment, the neutral sentiment, and the positive sentiment correspond to the negative polarity, the neutral polarity, and the positive polarity respectively.

The AI model 112 automatically identifies the possibility of the mental health condition of the user 102 when the at least one sentiment of the user 102 is found to be of the opposite polarity to that of the at least one predicted life situation of the high gravity situation. The opposite polarity is defined as the polarity of the life event being opposite of the initial sentiment of the user 102. For example, when the user 102 has a negative initial sentiment while the life situation extracted from their conversation with the AI chatbot has a positive polarity, or vice versa, then the sentiment is found to be opposite to the polarity.

The AI chatbot 110 quits identifying the possibility of the mental health condition of the user 102 when the priority of the at least one predicted life situation is mapped to the medium gravity situation, or the low gravity situation. The AI chatbot 110 terminates to identify the possibility of the mental health condition of the user 102 when the polarity of the initial mood of the user 102 and the at least one predicted life situation of high gravity situation are found to be the same. The possibility of the mental health condition may be an indicator of a psychological disorder such as bipolar disorder and/or schizophrenia.

Figure 2:
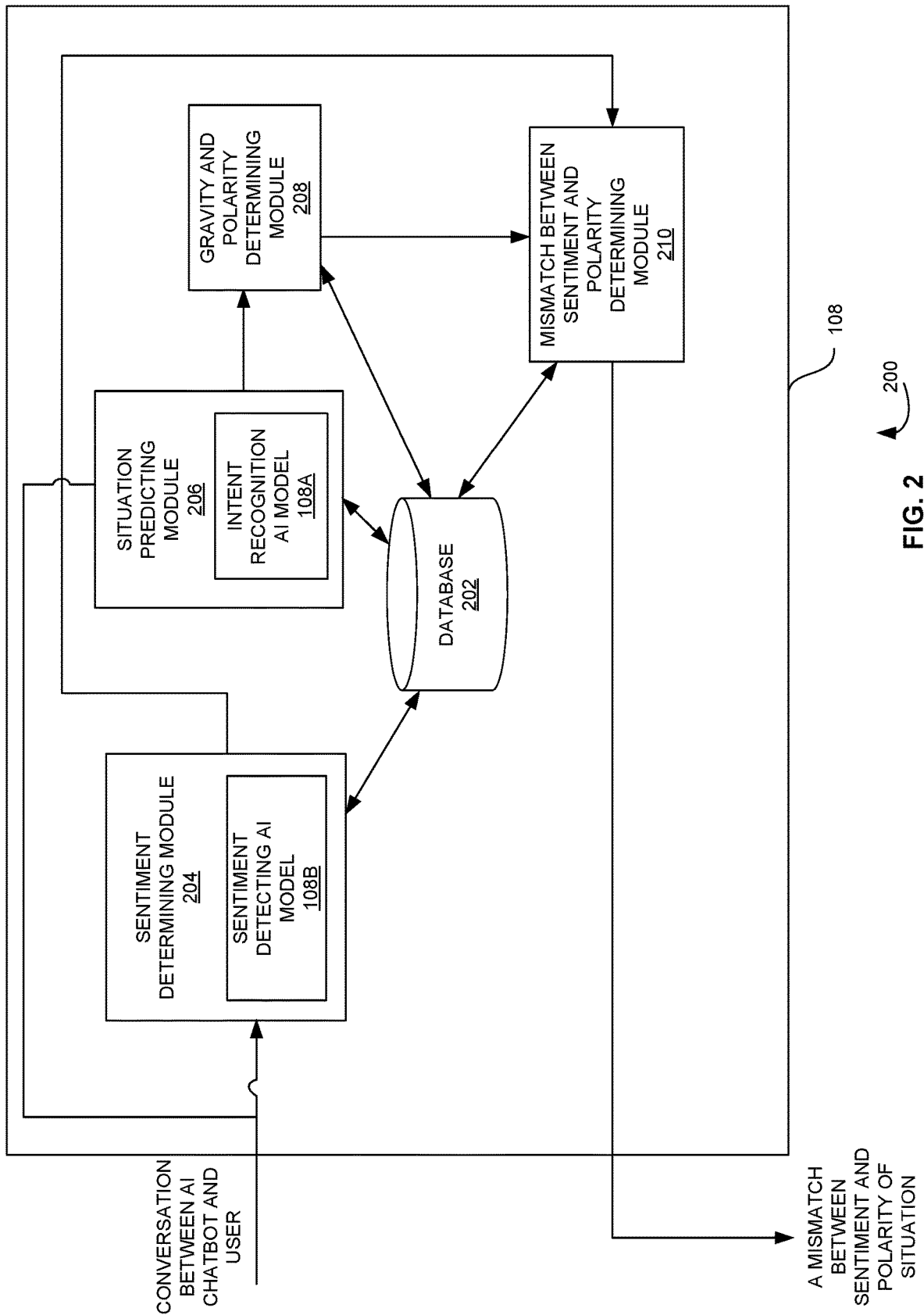
FIG. 2 is a block diagram of a server of FIG. 1 according to some embodiments herein.

FIG. 2 is a block diagram 200 of the server 108 of FIG. 1 according to some embodiments herein. The server 108 includes a database 202, a situation predicting module 206, the intent recognition AI model 112A, a sentiment determining module 204, the sentiment detecting AI model 112B, a gravity and polarity determining module 208, a mismatch between sentiment and polarity determining module 210. The sentiment determining module 204 determines at least one sentiment of the user 102 by checking an initial mood of the user 102. The initial mood of the user 102 is checked when the user 102 provides at least one of (i) a response from a set of pre-determined options for a question or (ii) text input that is asked by the AI chatbot 110 as how the user 102 is feeling. The sentiment-detecting AI model 112A classifies the at least one sentiment of the user as one of negative, neutral, and positive using at least one of (i) rule-based methods that have a large predefined set of words and the at least one sentiment associated with each word, and combine the at least one sentiment of each word in a sentence based on certain rules; or, (ii) machine learning classifiers trained on a large dataset of sentences labeled with associated sentiment so that the machine learning classifiers learn to classify the at least one sentiment on new sentences, unseen sentence.

The situation predicting module 206 predicts at least one life situation from the conversation between the AI chatbot 110 and the user 102 using the intent recognition AI model 112A. The intent recognition AI model 112A predicts the at least one life situation by (i) semantically matching statements of the conversation with representative statements of one or more life situations to obtain at least one semantic match, and (ii) assigning a confidence score to each semantic match. The database 202 stores the representative statements of one or more life situations.

The gravity and polarity determining module 208 determines a gravity, and a polarity of the at least one predicted life situation using a life events scale. The life events scale includes categories of events that could occur in a user's life. The events are mapped to a potential impact on a mental health of the user 102. The gravity and polarity determining module 208 maps the at least one predicted life situation into at least one of a high gravity situation, a medium gravity situation, or a low gravity situation. The gravity and polarity determining module 208 maps the at least one predicted life situation into at least one of a negative polarity, a neutral polarity, or a positive polarity using life event scale.

The mismatch between sentiment and polarity determining module 210 compares the at least one sentiment of the user 102 to the polarity of the at least one predicted life situation when the at least one predicted life situation is mapped to the high gravity. The at least one sentiment of the user and the polarity of the at least one life situation is selected from any of a positive, a neutral or a negative. The mismatch between sentiment and polarity determining module 210 automatically determines the mismatch between the at least one sentiment of the user and the polarity of the at least one life situation of high gravity. The mismatch between sentiment and polarity determining module 210 automatically identifies the possibility of the mental health condition of the user 102 when the at least one sentiment of the user 102 is found to be of the opposite polarity to that of the at least one predicted life situation of the high gravity situation.

The initial sentiment of the user 102 is compared to the polarity of the predicted life situation only when the predicted life situation is of high gravity because only in such cases, the mismatch of the sentiment and the polarity may be an indicator of a mental health condition. For example, there could be two situations with negative polarity—"I lost my glasses" and "I lost my pet". The gravity of the situation "I lost my glasses" is lesser than the gravity of the situation "I lost my pet". Hence, the comparison of the initial sentiment of the user 102 and the polarity of the predicted life situation will be done only in the latter situation, not in the former.

Similarly, there could be two events with positive polarity—"I had a good night's sleep", and "I am going to have a baby."However, the event "I had a good night's sleep" has lesser gravity than the event "I am going to have a baby.". Hence, the comparison of the initial sentiment of the user 102 and the polarity of the predicted life situation will be done only in the latter situation, not in the former.

Figure 3:
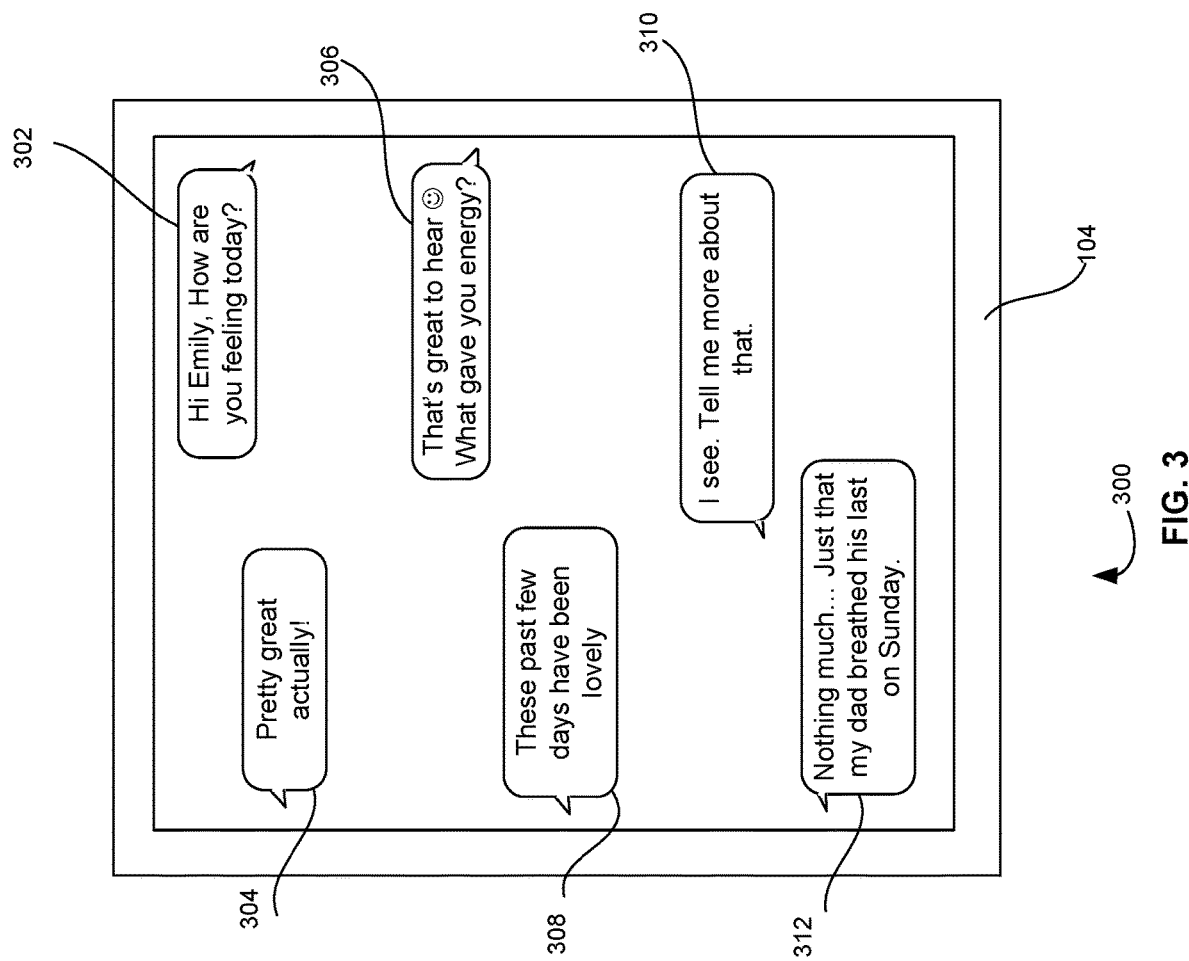
FIG. 3 is a mock-up screenshot of a user interface that illustrates a conversation between the AI chatbot and the user where a possibility of the mental health condition of the user is identified according to some embodiments herein.

FIG. 3 is a mock-up screenshot of a user interface 300 that illustrates the conversation between the AI chatbot 110 and the user 102 where a possibility of the mental health condition of the user 102 is identified according to some embodiments herein.

The AI chatbot 110 starts the conversation with an initial mood check of the user 102 by asking a question like "Hi Emily, how are you feeling today?" at 302. The user 102 may respond to the AI chatbot 110, for example, "Pretty great actually!" at 304. The sentiment-detecting AI model 112B detects an initial sentiment of the user 102 as a positive sentiment from this user response 304. The AI chatbot 110 then attempts to gather the context of the conversation by saying for example, "That's great to hear :) What gave you energy?" at 306.

The user 102 may respond at 308 to the AI chatbot 110 with, for example, "These past few days have been lovely.". The intent recognition AI model 112A tries to extract a life event, if any, from this response by looking for a semantic match among all the representative statements of various high-gravity life events. However, it doesn't find a match with any high-gravity life event with a high confidence score. Therefore, the AI chatbot 110 probes the user 102 further to gather context at 310 with, e.g., "I see. Tell me more about that." Further, the user 102 may respond with, e.g., "Nothing much . . . . Just that my dad breathed his last on Sunday." at 312. Here, the intent recognition AI model 112A finds a semantic match with a representative statement of the "loss of a family member" life event with a high confidence score. The gravity and the polarity of the detected life situation is determined using the life events scale. The gravity is found to be high and the polarity is found to be negative on the life events scale. As the initial mood was determined to have a positive sentiment, and the polarity of the detected high-gravity situation is determined to be negative, the possibility of a mental health condition is identified.

Figure 4:
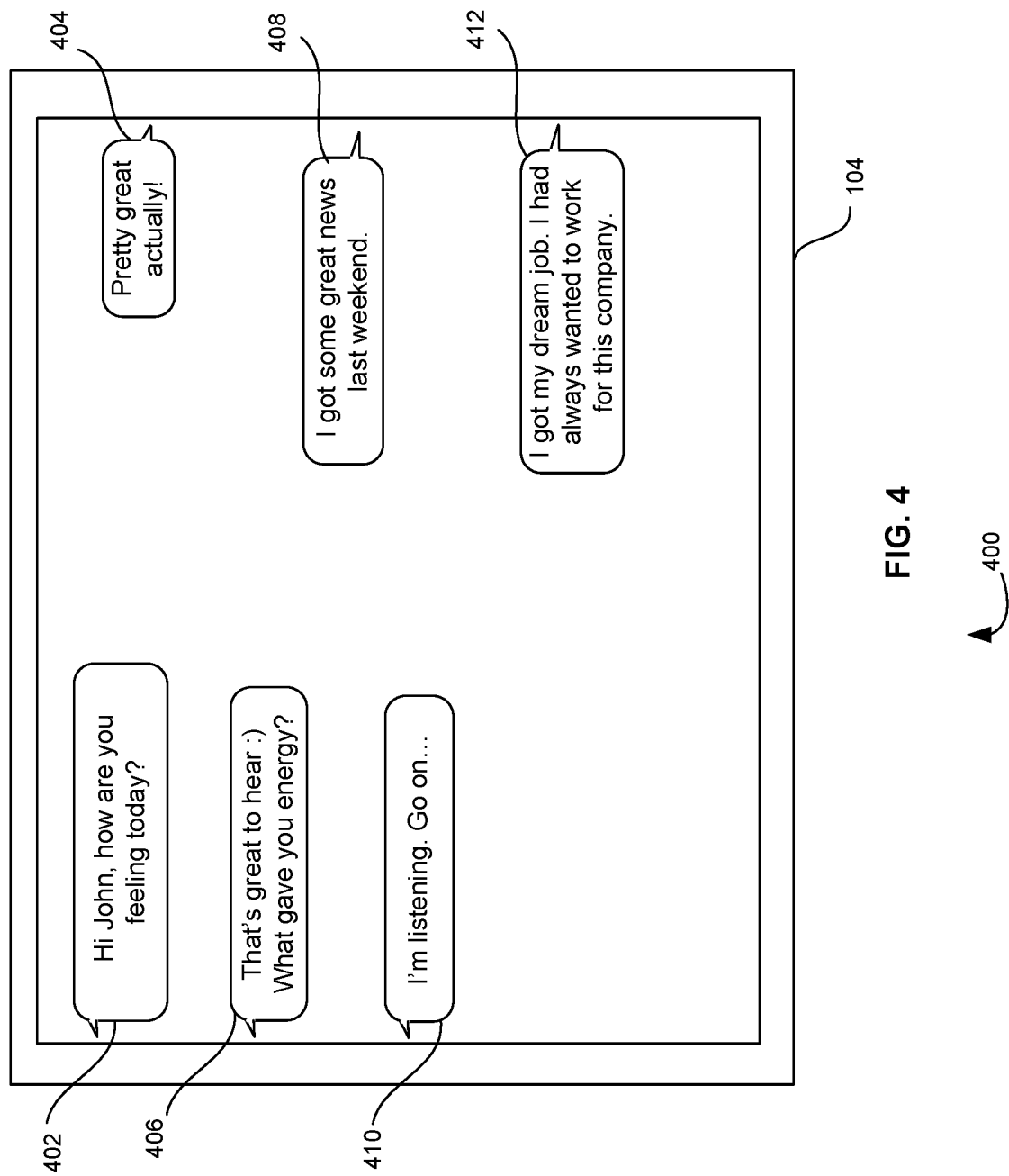
FIG. 4 is a mock-up screenshot of a user interface that illustrates a conversation between the AI chatbot and the user when no possibility of the mental health condition of the user is identified according to some embodiments herein.

FIG. 4 is a mock-up screenshot of a user interface 400 that illustrates the conversation between the AI chatbot 110 and the user 102 when no possibility of a mental health condition of the user 102 is identified according to some embodiments herein. The AI chatbot 110 starts the conversation with an initial mood check of the user 102 by asking a question like, "Hi John, how are you feeling today?" at 402. The user 102 may respond to the AI chatbot 110 with, for example, "Pretty great actually!" at 404. The sentiment-detecting AI model 112B detects the initial sentiment of the user 102 as a positive sentiment. The AI chatbot 110 then attempts to gather the context of the conversation by saying for example, "That's great to hear :) What gave you energy?" at 406.

The user 102 may respond at 408 to the AI chatbot 110 with, for example, "I got some great news last weekend.". The intent recognition AI model 112A tries to extract a life event, if any, from this response by looking for a semantic match among all the representative statements of various high-gravity life events. However, it doesn't find a match with any high-gravity life event with a high confidence score. Therefore, the AI chatbot 110 further probes the user 102 further to gather context at 410 with, e.g., "I'm listening. Go on . . . ". Further, the user 102 may respond with, e.g., "I got my dream job. I had always wanted to work for this company." at 412. Here, the intent recognition AI model 112A finds a semantic match with a representative statement of the "employment job gain" life event. The gravity and the polarity of the detected life situation is determined using the life events scale. The gravity is found to be of high and the polarity is found to be positive on the life events scale. As the initial mood was determined to have a positive sentiment, and the polarity of the detected high-gravity situation is determined to be positive, there is no possibility of a mental health condition being identified.

FIG. 5A is a mock-up screenshot of a user interface 500 that illustrates a conversation between the AI chatbot 110 and the user 102 when the user 102 didn't share enough context according to some embodiments herein. The context of the conversation is about why they were feeling the way they were, despite multiple prompts, which resulted in the intent recognition AI model 112A being unable to extract a life situation from the user 102 conversation with enough confidence. In such a scenario, identification of the possibility of a mental health condition of the user 102 is not possible. The AI chatbot 110 starts the conversation with an initial mood check of the user 102 by asking a question like, "Hi Nick, good to see you again. How are you feeling today?" at 502. The user 102 may respond to the AI chatbot 110 with, for example, "Not so great . . . " at 504. The sentiment-detecting AI model 112B detects the initial sentiment of the user 102 as a negative sentiment. The AI chatbot 110 then attempts to gather the context of the conversation by saying for example, "I'm sorry to hear that. What's upsetting you?" at 506. The user 102 may respond at 508 to the AI chatbot 110 e.g., "Things haven't been good lately . . . ". The intent recognition AI model 112A doesn't match any high-gravity life event with a high confidence score. Thus, the AI chatbot 110 probes the user 102 further at 510 with, for example, "I'm listening. Go on . . . ". Further, the user 102 may respond, e.g., "I don't feel like doing anything." at 512. Again, the intent recognition AI model 112A doesn't match any high-gravity life event with a high confidence score. The AI chatbot 110 makes one last attempt to gather context at 514, e.g., "Tell me more, Nick. Venting to me will help.". Further, the user 102 may respond, e.g., "I don't know . . . I can't explain. It's my girlfriend." at 516. Here, the intent recognition AI model 112A finds a semantic match with relationship-related life events but with a low confidence score. Hence, no conclusive life event could be detected in the user statements even after three attempts. The AI chatbot 110, thus, quits trying to identify the possibility of a mental health condition of the user 102, and continues the conversation normally.

Figure 5B:
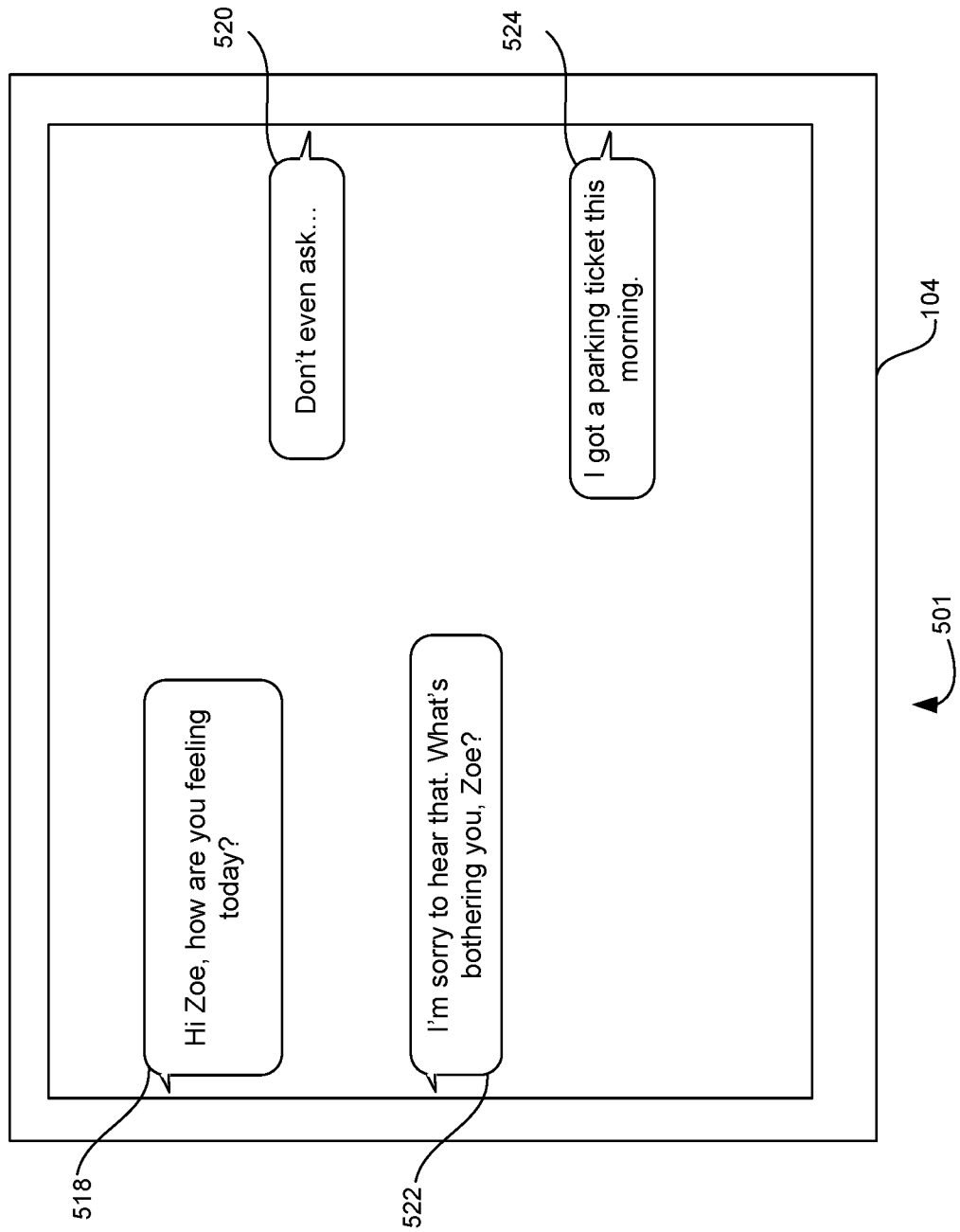
FIG. 5B is a mock-up screenshot of a user interface that illustrates a conversation between the AI chatbot and the user where a low or medium-gravity life event was extracted from the user messages according to some embodiments herein.

FIG. 5B is a mock-up screenshot of a user interface 501 that illustrates a conversation between the AI chatbot 110 and the user 102 where a low or medium-gravity life event was extracted from the user messages according to some embodiments herein. In the absence of a high-gravity event, an attempt to predict the possibility of a mental health condition of the user 102 is not made because even if the initial sentiment of the user is opposite of the polarity of the extracted life event, it may not be a strong indicator of a mental health condition. The mock-up screenshot of the user interface 501 illustrates the conversation between the AI chatbot 110 and the user 102 when a low-gravity life event related to financial loss was predicted from the user message, "I got a parking ticket this morning." In such a scenario, no attempt to predict the possibility of a mental health condition of the user 102 is made according to some embodiments herein.

Figure 6:
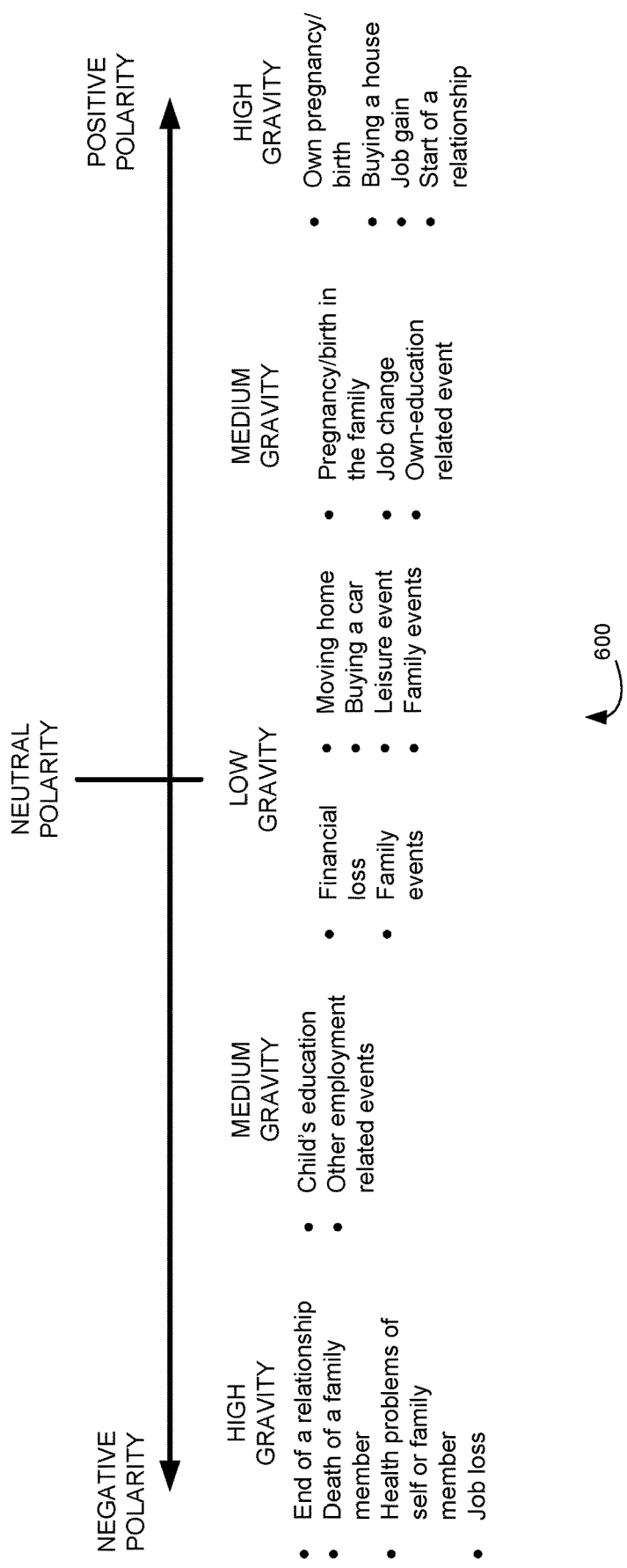
FIG. 6 is an exemplary life events scale for determining a gravity and a polarity of a situation according to some embodiments herein.

FIG. 6 is an exemplary life events scale 600 for determining a gravity and a polarity of a situation according to some embodiments herein. The exemplary life events scale 600 depicts mapping of the high, medium, low gravities corresponding to positive and negative polarities. For example, the negative polarity corresponds to high, medium, low gravities. The exemplary life events scale 600 includes life events and situations that are mapped to a potential impact on health of the user 102. The life events are defined as a social experience or change that has a defined time of occurrence and a psychological impact on the user. In some embodiments, major life events are out-of-the-ordinary, demanding events that have the capacity to change the patterns of life. The history of life events and the occurrence of major life events may be closely related to the user's level of stress and happiness, and in turn, to their mental health. In some embodiments, the exemplary life events scale 600 is a comprehensive list of such external events and situations, mapped to their potential impact (positive or negative) on the user's health.

Some exemplary life event scales are the Holmes & Rahe Stress Inventory, the Life Events and Difficulties Schedule (LEDS), the Computerised Life Events and Assessment Record (CLEAR), the Pleasant Events Schedule (PES), and the General Happiness Question (GHQ) scale developed using the British Household Panel Survey (BHPS) data, among others. In some embodiments, the exemplary life events scale 600 is determined by conducting a survey over a certain population and collecting self-reported data on the occurrence of various life events over a predefined time period. During this time period, either the participants' health is monitored or they self-report their perceived degree of stress or happiness caused by these life events, and a correlation is derived between the stress/happiness scores reported and the participants' health. Several statistical analyses are then done on the scales to verify the reliability and robustness of the exemplary life events scale 600.

Figure 7:
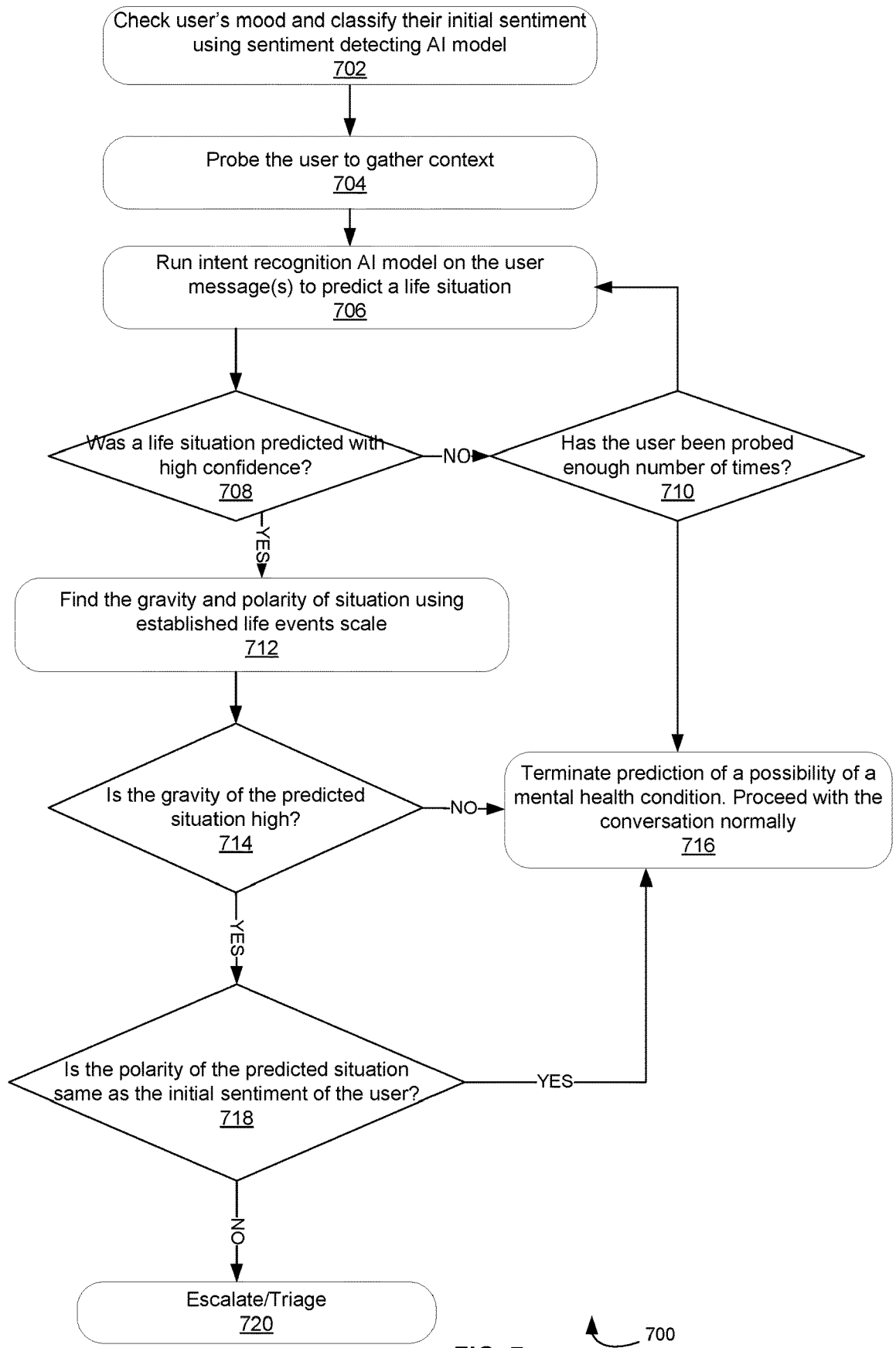
FIG. 7 is a flowchart that illustrates a method for determining a possibility of a mental health condition of a user using an artificial intelligence (AI) model according to some embodiments herein.

FIG. 7 is a flowchart that illustrates a method for determining a possibility of a mental health condition of the user 102 using the artificial intelligence (AI) model 112 according to some embodiments herein. At a step 702, the user's initial sentiment is checked by monitoring a conversation between the AI chatbot 110 and the user 102 using the sentiment detecting AI model 112B. At a step 704, context is gathered by probing the user 102 about why they are feeling the way they are. At the step 706, a life situation is extracted from the user's response by running an intent recognition AI model 112A on the user's messages. At the step 708, it is checked if the life situation is predicted with high confidence or not. At the step 710, if the life situation is not predicted with a high confidence score, it is checked whether the user 102 has been probed into enough number of times. At the step 712, a gravity and a polarity of the extracted life situation is found using a life events scale if the life situation is predicted with the high confidence score. At the step 714, it is checked if the gravity of the extracted situation is high according to the life events scale. At the step 716, if the gravity of the predicted situation is not high, prediction of the possibility of the mental health condition of the user 102 is terminated and the conversation proceeds normally. However, if the gravity of the predicted situation is high, at the step 718, the polarity of the extracted situation according to the life events scale is compared with the initial sentiment of the user 102. At the step 720, the user 102 is triaged if the polarity of the extracted situation is found to be opposite of the initial sentiment of the user 102. However, if the polarity of the extracted situation is the same as the initial sentiment of the user 102, then it is concluded that there is no possibility of a mental health condition and the conversation continues normally.

Figure 8:
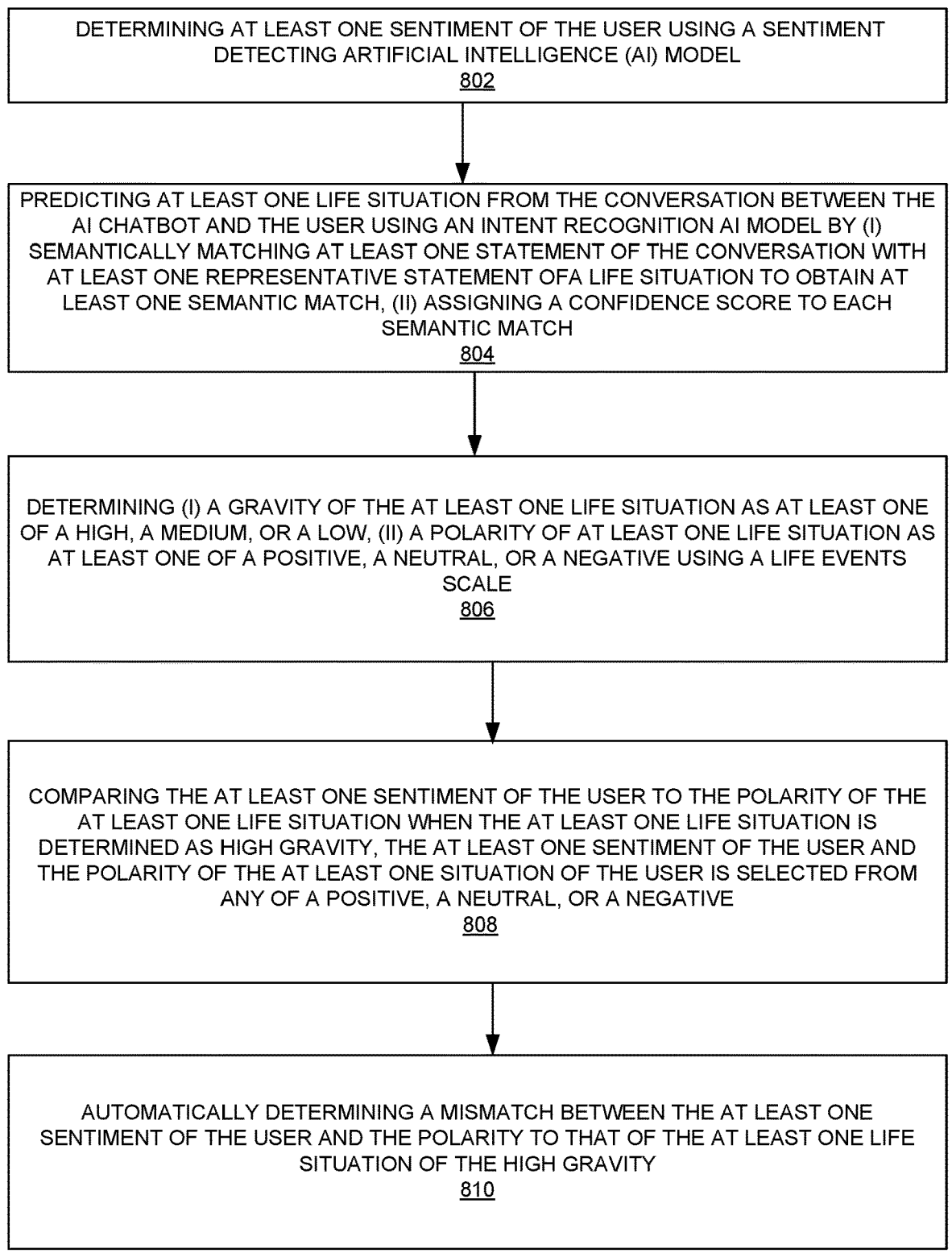
FIG. 8 is a flow diagram that illustrates a method for automatically determining a mismatch between a sentiment and a polarity of a life situation using an Artificial Intelligence (AI) model during a conversation with an AI chatbot according to some embodiments herein.

FIG. 8 is a flow diagram that illustrates a method for automatically determining a mismatch between a sentiment and a polarity of a life situation using the Artificial Intelligence (AI) model 112 during a conversation with the AI chatbot 110 according to some embodiments herein. At a step 802, the method 800 includes determining at least one sentiment of the user using the sentiment detecting artificial intelligence (AI) model. At a step 804, the method 800 includes predicting at least one life situation from the conversation between the AI chatbot and the user using an intent recognition AI model by (i) semantically matching at least one statement of the conversation with at least one representative statement of a life situation to obtain at least one semantic match, and (ii) assigning a confidence score to the at least one semantic match. At a step 806, the method 800 includes determining (i) a gravity of the at least one life situation as at least one of high, medium or low, and (ii) a polarity of the at least one life situation as at least one of negative, neutral or positive using a life events scale. At a step 808, the method 800 includes comparing the at least one sentiment of the user to the polarity of the at least one life situation when the at least one life situation is determined as the high, the at least one sentiment of the user and the polarity of the at least one life situation is selected from any of a positive, a neutral, or a negative. At a step 810, the method 800 includes automatically determining the mismatch between the at least one sentiment of the user and the polarity of the at least one life situation of the high gravity situation.

The embodiments herein may include a computer program product configured to include a pre-configured set of instructions, which when performed, can result in actions as stated in conjunction with the methods described above. In an example, the pre-configured set of instructions can be stored on a tangible non-transitory computer readable medium or a program storage device. In an example, the tangible non-transitory computer readable medium can be configured to include the set of instructions, which when performed by a device, can cause the device to perform acts similar to the ones described here. Embodiments herein may also include tangible and/or non-transitory computer-readable storage media for carrying or having computer executable instructions or data structures stored thereon.

Generally, program modules utilized herein include routines, programs, components, data structures, objects, and the functions inherent in the design of special-purpose processors, etc. that perform particular tasks or implement particular abstract data types. Computer executable instructions, associated data structures, and program modules represent examples of the program code means for executing steps of the methods disclosed herein. The particular sequence of such executable instructions or associated data structures represents examples of corresponding acts for implementing the functions described in such steps. The embodiments herein can include both hardware and software elements. The embodiments that are implemented in software include but are not limited to, firmware, resident software, microcode, etc. A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem, and Ethernet cards are just a few of the currently available types of network adapters.

Figure 9:
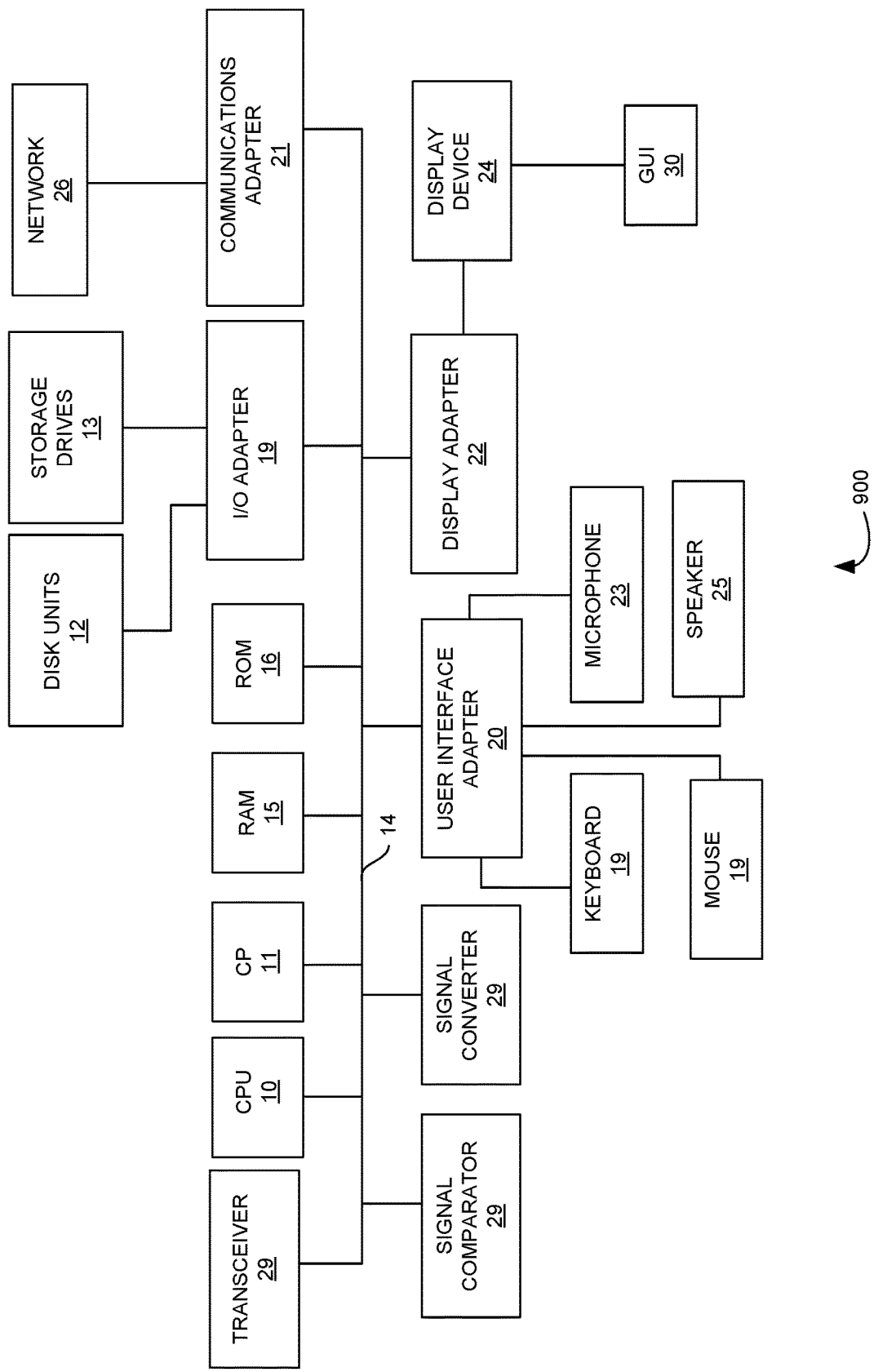
FIG. 9 is a block diagram of a schematic diagram of a device used in accordance with embodiments herein.

A representative hardware environment for practicing the embodiments herein is depicted in FIG. 9, with reference to FIGS. 1 through 8. This schematic drawing illustrates a hardware configuration of a server 108/ a computer system/ a user device 104 in accordance with the embodiments herein. The user device 104 includes at least one processing device 10 and a cryptographic processor 11. The special-purpose CPU 10 and the cryptographic processor (CP) 11 may be interconnected via system bus 14 to various devices such as a random access memory (RAM) 15, read-only memory (ROM) 16, and an input/output (I/O) adapter 17. The I/O adapter 17 can connect to peripheral devices, such as disk units 12 and tape drives 13, or other program storage devices that are readable by the system. The user device 104 can read the inventive instructions on the program storage devices and follow these instructions to execute the methodology of the embodiments herein. The user device 104 further includes a user interface adapter 20 that connects a keyboard 18, mouse 19, speaker 25, microphone 23, and/or other user interface devices such as a touch screen device (not shown) to the bus 14 to gather user input. Additionally, a communication adapter 21 connects the bus 14 to a data processing network 26, and a display adapter 22 connects the bus 14 to a display device 24, which provides a graphical user interface (GUI) 30 of the output data in accordance with the embodiments herein, or which may be embodied as an output device such as a monitor, printer, or transmitter, for example. Further, a transceiver 27, a signal comparator 28, and a signal converter 29 may be connected with the bus 14 for processing, transmission, receipt, comparison, and conversion of electric or electronic signals.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A processor-implemented method for automatically determining a mismatch between a sentiment and a polarity of a life situation using an Artificial Intelligence (AI) model during a conversation with an AI chatbot, comprising:
    determining at least one sentiment of the user using a sentiment detecting AI model;
    predicting at least one life situation from the conversation between the AI chatbot and the user using an intent recognition AI model, wherein predicting the at least one life situation comprises (i) semantically matching at least one statement of the conversation with at least one representative statement of a life situation using the intent recognition AI model to obtain at least one semantic match, and (ii) assigning a confidence score to the at least one semantic match;
    determining (i) a gravity of the at least one life situation as at least one of high, medium or low, and (ii) a polarity of the at least one life situation as at least one of negative, neutral or positive using a life events scale;
    comparing the at least one sentiment of the user to the polarity of the at least one life situation when the gravity of the at least one life situation is determined as high, wherein the at least one sentiment of the user and the polarity of the at least one life situation is selected from any of a positive, a neutral or a negative; and
    automatically determining the mismatch between the at least one sentiment of the user and the polarity of the at least one life situation of high gravity.

2. The processor-implemented method of claim 1, further comprising,
    determining the at least one life situation that is semantically close to a statement made by the user when (i) the confidence score of the at least one semantic match is above a threshold, and (ii) the at least one situation is determined to be the high gravity.

3. The processor-implemented method of claim 2, further comprising
    obtaining more context about the user's feeling when the intent recognition AI model is unable to predict the at least one life situation due to confidence scores of all semantic matches of the statement made by the user being less than the threshold.

4. The processor-implemented method of claim 1, wherein the AI chatbot stops determining the mismatch when the at least one sentiment of the user and the polarity of the at least one life situation of the high gravity are found to be the same.

5. The processor-implemented method of claim 1, wherein the AI chatbot stops determining the mismatch when the gravity of the at least one life situation is determined as the medium, or the low.

6. The processor-implemented method of claim 1, wherein the gravity of the at least one life situation is a measure of how much the at least one life situation is likely to influence the mood of the user, wherein the polarity of the at least one life situation indicates whether the at least one life situation is likely to influence the mood of the user positively, negatively, or not at all.

7. The processor-implemented method of claim 1, wherein the sentiment-detecting AI model classifies the at least one sentiment of the user as one of negative, neutral, and positive using at least one of (i) rule-based methods that have a large predefined set of words and the at least one sentiment associated with each word, to combine the at least one sentiment of each word in a sentence based on certain rules; or, (ii) machine learning classifiers trained on a large dataset of sentences labeled with associated sentiment so that the machine learning classifiers learn to classify the at least one sentiment on new sentences, unseen sentences.

8. The processor-implemented method of claim 1, wherein the life events scale comprises categories of events that could occur in a user's life, wherein the events are mapped to a potential impact on a mental health of the user.

9. The processor-implemented method of claim 1, wherein the at least one sentiment of the user is determined from at least one of (i) when the user provides a response from a set of pre-determined options for a question that is asked by the AI chatbot as how the user is feeling or (ii) an input text provided by the user.

10. One or more non-transitory computer readable storage mediums storing one or more sequences of instructions, which when executed by one or more processors, causes a method for automatically determining a mismatch between a sentiment and a polarity of a life situation using an Artificial Intelligence (AI) model during a conversation with an AI chatbot, comprising:
    determining at least one sentiment of the user using a sentiment detecting AI model;
    predicting at least one life situation using an intent recognition AI model from the conversation between the AI chatbot and the user, wherein predicting the at least one life situation comprises (i) semantically matching at least one statement of the conversation with at least one representative statement of a life situation using the intent recognition AI model to obtain at least one semantic match, and (ii) assigning a confidence score to the at least one semantic match;
    determining (i) a gravity of the at least one life situation as at least one of high, medium or low, and (ii) a polarity of the at least one life situation as at least one of negative, neutral or positive using a life events scale;
    comparing the at least one sentiment of the user to the polarity of the at least one life situation when the gravity of the at least one life situation is determined as high, wherein the at least one sentiment of the user and the polarity of the at least one life situation is selected from any of a positive or a negative; and
    automatically determining the mismatch between the at least one sentiment of the user and the polarity of the at least one life situation of high gravity.

11. The one or more non-transitory computer readable storage mediums storing the one or more sequences of instructions of claim 10, further comprising determining the at least one life situation that is semantically close to a statement by the user when (i) the confidence score of the at least one semantic match is above a threshold, and (ii) the at least one situation is mapped to the high gravity situation.

12. The one or more non-transitory computer readable storage mediums storing the one or more sequences of instructions of claim 10, further comprising obtaining more context when the intent recognition AI model is unable to predict the at least one life situation due to confidence scores of all semantic matches of the statement by the user are less than the threshold.

13. A system for automatically determining a mismatch between a sentiment and a polarity of a life situation using an Artificial Intelligence (AI) model during a conversation with an AI chatbot comprising:
    a device processor; and
    a non-transitory computer readable storage medium storing one or more sequences of instructions, which when executed by the device processor, causes a method by performing the steps of:
        determining at least one sentiment of the user using a sentiment detecting AI model;
        predicting at least one life situation using an intent recognition AI model from the conversation between the AI chatbot and the user, wherein predicting the at least one life situation comprises (i) semantically matching at least one statement of the conversation with at least one representative statement of a life situation using the intent recognition AI model to obtain at least one semantic match, and (ii) assigning a confidence score to the at least one semantic match;
        determining (i) a gravity of the at least one life situation as at least one of high, medium or low, and (ii) a polarity of the at least one life situation as at least one of negative, neutral or positive using a life events scale;
        comparing the at least one sentiment of the user to the polarity of the at least one life situation when the gravity of the at least one life situation is determined as high, wherein the at least one sentiment of the user and the polarity of the at least one life situation is selected from any of a positive or a negative; and
        automatically determining the mismatch between the at least one sentiment of the user and the polarity of the at least one life situation of high gravity.

14. The system of claim 13, wherein the device processor is further configured to determine the at least one life situation that is semantically close to a statement by the user when (i) the confidence score of the at least one semantic match is above a threshold, and (ii) the at least one situation is mapped to be the high gravity.

15. The system of claim 14, wherein the AI chatbot obtains more context when the intent recognition AI model is unable to predict the at least one life situation due to confidence scores of all semantic matches of the statement by the user are less than the threshold.

16. The system of claim 13, wherein the AI chatbot stops to determine the mismatch when the at least one sentiment of the user and the polarity of the at least one life situation of the high gravity situation are found to be same.

17. The system of claim 13, wherein the AI chatbot stops to determine the mismatch when the gravity of the at least one life situation is determined as the medium, or the low.

18. The system of claim 13, wherein the gravity of the at least one life situation is a measure of how much the at least one life situation is likely to influence the mood of the user, wherein the polarity of the at least one life situation indicates whether the at least one life situation is likely to influence the mood of the user positively, negatively, or not at all.

19. The system of claim 13, wherein the sentiment-detecting AI model classifies the at least one sentiment of the user as one of negative, neutral, and positive using at least one of (i) rule-based methods that have a large predefined set of words and the at least one sentiment associated with each word, to combine the at least one sentiment of each word in a sentence based on certain rules; or, (ii) machine learning classifiers trained on a large dataset of sentences labeled with associated sentiment so that the machine learning classifiers learn to classify the at least one sentiment on new sentences, unseen sentences.

20. The system of claim 13, wherein the life events scale comprises categories of events that could occur in a user's life, wherein the events are mapped to a potential impact on a mental health of the user.

\* \* \* \* \*